United States Patent [19]
Grabo et al.

[11] Patent Number: 5,573,786
[45] Date of Patent: Nov. 12, 1996

[54] PREPARATION FOR SKIN AND MUCOUS MEMBRANE

[75] Inventors: Michael Grabo; Christian Stfähli, both of Basel; Rudolf Meyer, Wahlen; René Glauser, Basel, all of Switzerland; Murray Weiner, Cincinnati, Ohio

[73] Assignee: Solco Basel AG, Basel, Switzerland

[21] Appl. No.: 264,687

[22] Filed: Jun. 23, 1994

[30] Foreign Application Priority Data

Jun. 23, 1993 [CH] Switzerland .............................. 1887/93

[51] Int. Cl.$^6$ ....................................................... A61K 7/48
[52] U.S. Cl. ........................... 424/718; 510/131; 510/159
[58] Field of Search ........................ 424/718; 252/DIG. 5

[56] References Cited

U.S. PATENT DOCUMENTS 4,595,591  6/1986  Mardi ...................................... 424/127

FOREIGN PATENT DOCUMENTS 0026532  4/1981  European Pat. Off. .

OTHER PUBLICATIONS

*European Drug Index, Second Edition*, edited by Muller et al., 1992, p. 1096.

Heaton, et al., *Clinical Pharmacology and Therapeutics*, "The Revival of Nitric Acid for the Treatment of Anogenital Warts", vol. 54, No. 1, pp. 107–111 (1993).

*Primary Examiner*—C. Warren Ivy
*Assistant Examiner*—Evelyn Huang
*Attorney, Agent, or Firm*—Wenderoth, Lind & Ponack

[57] ABSTRACT

By reacting 1–5.5M nitric acid with from 45 to 170 mmol of primary $C_1$-$C_5$-alkanol per 1 of nitric acid, an improved preparation is obtained for the local treatment of changes in skin and mucous membrane and of infections of the skin and mucous membrane. The preparation comprises 1–5.5M nitric acid, not more than 170 mmol of $C_1$-$C_5$-alkanoic acid per 1 of solution, and nitrate reduction products in a concentration corresponding to from 0.1 to 6 mg of nitrite per ml of solution. The preparation is notable for a good activity and a low risk of side effects.

18 Claims, 5 Drawing Sheets

PREPARATION FOR SKIN AND MUCOUS MEMBRANE

The invention relates to a new preparation, based on an aqueous solution of nitric acid which contains nitrate reduction products, for the local treatment of changes in skin and mucous membrane, in particular of superficial, benign changes in skin and mucous membrane, both large and small in area, and of superficial infections of the skin and mucous membrane, and to a process for the production of this preparation.

For centuries now, the "burning out" of skin defects, warts and the like has entailed the use of caustic preparations, in particular of strong acids. In this context a more or less specific place in the dermatologists' "medicine cabinet" has become occupied in particular by salicylic acid, by concentrated forms of nitric acid and by certain haloacetic acids, whereas hydrochloric acid is seldom used. Treatment with caustic preparations is generally painful and in many cases is known to leave more or less unsightly scars.

Furthermore, to combat warts, lactic acid, oxalic acid and acetic acid have also been proposed. The keratolytic action of these acids, however, is low, and they are therefore almost always used in combination with salicylic acid (German Auslegeschrift 1 266 448).

On the other hand, to combat warts and other skin defects it was also proposed, in the 19th century, to use various metal salts, including copper salts such as the acetate or the sulphate, lead salts in combination with zinc sulphate, copper sulphate together with acetic acid, and also salts of antimony, arsenic, chromium, mercury, silver, zinc and cadmium. Among these salts, only zinc chloride, in combination with trichloroacetic acid—Mohs' method—gained a passing significance for the treatment of skin cancer.

For the local treatment of superficial changes in skin and mucous membrane, EP-A-26 532 recommended the use of a 6–10M aqueous solution of nitric acid, containing metal nitrite or nitrous acid in a quantity corresponding to from 0.01 to 5 mg, preferably from 0.1 to 0.5 mg, of nitrite per ml of solution. As disclosed in EP-A-26 532, such preparations give—measured with respect to skin discolouration—a similarly rapid chemical reaction to that of concentrated nitric acid, but without the vigorously caustic action, breaking up all tissue indiscriminately, of this and other strong acids. Under the action of the preparations the integumental proteins are in fact denatured in situ, and the anatomical structure is intravitally fixed without injury (mummification).

For the composition and action of the known preparations, it proved particularly advantageous to produce the preparations by adding oxidizable organic carboxylic acids to nitric acid or possibly to add such oxidizable organic carboxylic acids to the preparations. The oxidizable carboxylic acids, such as oxalic acid, lactic acid, glycolic acid, glyoxylic acid, malic acid and the like react with the nitric acid to form a series of products, in particular nitrate reduction products such as nitrous gases and nitrous acid, and also condensation products such as O-nitrile and O-nitrosyl derivatives. The preparations obtained by this oxidative method result in particular in an improved activity over longer periods of time. It is not known specifically which of the reaction products are primarily responsible for the clinically useful properties, although the activity is lost if there is too great a fall in the content of the reaction products which can be measured as nitrite.

The oxidizable organic carboxylic acids react with 6–10M nitric acid to form nitrous gases, carbon dioxide etc. According to the disclosure of EP-A-26 532, therefore, it is important that preparations produced by this method are not hermetically sealed but are stored in a container provided with a loose closure. To this end, EP-A-26 532 recommends the use of a mixture of carboxylic acids which can be oxidized at different rates, for example the use of a mixture of pyruvic acid, lactic acid and oxalic acid, to enable compensation for a decrease in the nitrite content which may occur as a result of the container being stored or opened. In practice, however, it is evident that the reaction of the oxidizable carboxylic acids, which is required for the subsequent formation of nitrite, takes place too slowly at room temperature.

Corresponding preparations are marketed by the Applicant Company under the names Solcoderm and Solcogyn and have proved themselves in practice, provided that they have a sufficient nitrite concentration.

The known preparations, however, have the disadvantage that the rates of reaction of the oxidizable carboxylic acids are heavily dependent on temperature. As a result of this, the nitrite concentration may be subject to considerable fluctuations, depending on the storage temperature and storage time. Adequate reproducibility with respect to the composition and action of the preparations is therefore only ensured if the recommended storage temperature and the use-by dates indicated are observed as accurately as possible. Otherwise, the nitrite concentration may in some circumstances decrease to such an extent that the preparations become inactive. It has been observed that preparations of this kind which have become inactive present an increased danger of side effects and may, for example, lead to ulcerations on healthy skin.

It has now been found that an equally good and reproducible activity can be achieved, without the disadvantages of the known preparations, with a new preparation which, surprisingly, at the same time permits a further reduction in the concentration of nitric acid. In addition, the new preparation is particularly simple to prepare, from 1–5.5M aqueous nitric acid and a primary $C_1$-$C_5$-alkanol in a quantity of from 45 to 170 mmol per l of nitric acid, and is of simplified composition. The latter fact is an additional advantage since preparations which consist of numerous active substances are generally regarded, in modern-day pharmacology, as being problematic.

The preparation according to the invention for the local treatment of superficial changes in skin and mucous membrane comprises 1–5.5M aqueous nitric acid, nitrate reduction products in a concentration corresponding to from 0.1 to 6 mg of nitrite per ml of solution, and $C_1$-$C_5$-alkanoic acid in a concentration of not more than 170 mmol per l of solution. The preparations according to the invention generally contain at least approximately 5 mmol of $C_1$-$C_5$-alkanoic acid, for example from 45 to 170 mmol of $C_1$-$C_5$-alkanoic acid, per l of solution. Those preparations which are generally preferred contain at least approximately 9 and not more than approximately 90 mmol of $C_1$-$C_5$-alkanoic acid per l of solution.

In the context of the present inventions, indications of the nitrite concentration relate in each case to values obtained by the method described by N. G. Bunton, N. T. Crosby and S. J. Patterson in Analyst 94, 585 (1969), by reaction with sulphanilic acid and 1-naphthylamine followed by photometric determination. In this method other nitrate reduction products present in the solution, such as nitrous gases, are converted to nitrite and likewise detected. The nitrite concentrations given therefore signify in each case the nitrite concentration which is equivalent to the overall concentration of nitrate reduction products.

According to the invention, the new preparation can be produced simply by reacting 1–5.5M aqueous nitric acid with a primary $C_1$-$C_5$-alkanol in a quantity of from 45 to 170 mmol per l of nitric acid. Indeed it has been found, surprisingly, that primary $C_1$-$C_5$-alkanols react rapidly and completely in the aqueous nitric acid even at room temperature or at elevated temperature, and are thereby converted to $C_1$-$C_5$-alkanoic acids and carbon dioxide, with the simultaneous formation of an effective series of nitrate reduction products. The reaction can be preferably at a temperature of from approximately 20° to 60° C.

A $C_2$-$C_5$-alkanol such as ethanol or 1-propanol is preferably used. Particular preference is given to ethanol, which reacts completely by simply mixing with the nitric acid at room temperature, and is thereby converted to the keratolytically active acetic acid (and, partially, to carbon dioxide). The alkanoic acid present in the preparation according to the invention is thereby preferably a $C_2$-$C_5$-alkanoic acid, especially acetic acid.

BRIEF DESCRIPTION OF DRAWINGS

FIG. 1 shows, in graph form, the nitrite concentration of the known preparation, Solcoderm, as a function of the storage temperature and storage time. In order to determine this function the commercial preparation, which in the initial mixture contains 625.2 mg of 65% strength nitric acid, 41.5 mg of 98% strength acetic acid, 57.4 mg of oxalic acid dihydrate, 4.5 mg of lactic acid and 48 μg of copper(II) nitrate trihydrate per ml of solution, is stored in hermetically sealed glass ampoules at different temperatures over several months, and the nitrite concentration is measured at regular intervals. As the results shown in FIG. 1 indicate, the nitrite concentration may—depending on the temperature—be subject to considerable fluctuations, making its safe handling considerably more difficult. In particular, at a low storage temperature of 5° C., a reduction in the nitrite content and thus a loss of activity is observed. On the other hand, at temperatures of 30° C. and 45° C. a sharp increase is noted in the nitrite concentration, which may affect the storage life as a result of the accelerated reaction of the carboxylic acids.

In contrast to the known preparation, the preparations according to the invention possess a defined and reproducible composition by virtue of the rapid and complete reaction, thereby very largely eliminating uncertainties with regard to activity.

However, leaving the preparations standing open leads, in the case of both the preparations according to the invention and the known preparations, to a distinct decrease in the content of nitrate reduction products within a few hours, as a result of nitrous gases being given off. Therefore, the preparations according to the invention are preferably stored in containers with a gastight closure, for example in glass ampoules, or if required are not prepared until shortly before application.

Preparations according to the invention which are present in a container with a gastight closure, preferably in a sealed ampoule, possess a constant and essentially temperature-independent composition and action, and have virtually unlimited storage lives. In addition, storage under gastight closure is significantly facilitated by the fact that, in contrast to the known preparations, there is no continuous formation of carbon dioxide and nitrous gases over a prolonged period. Consequently, the possible danger of excessive pressures forming during storage, which could in extreme cases, at elevated storage temperatures, lead to the ampoules bursting or to the solution emerging explosively on opening, is reduced virtually to zero for the preparations according to the invention.

The production of preparations with a gastight seal can be carried out in principle by first producing, as described above, the preparation and then sealing this preparation in a gastight manner in a suitable container. The procedure is preferably such that the 1–5.5M nitric acid and the primary $C_1$-$C_5$-alkanol are mixed at a temperature below the reaction temperature, preferably at least 10° C. below the reaction temperature (e.g. at approximately 0° C.), the mixture is sealed in a gastight manner in a suitable container, preferably in an ampoule, and the mixture is then heated to reaction temperature or above. If ethanol is used, then the components are preferably mixed at a temperature of not more than 10° C., for example at 0°–5° C. and the mixture is subsequently reacted at a temperature of preferably from approximately 20° to 40° C.

Figure 1:
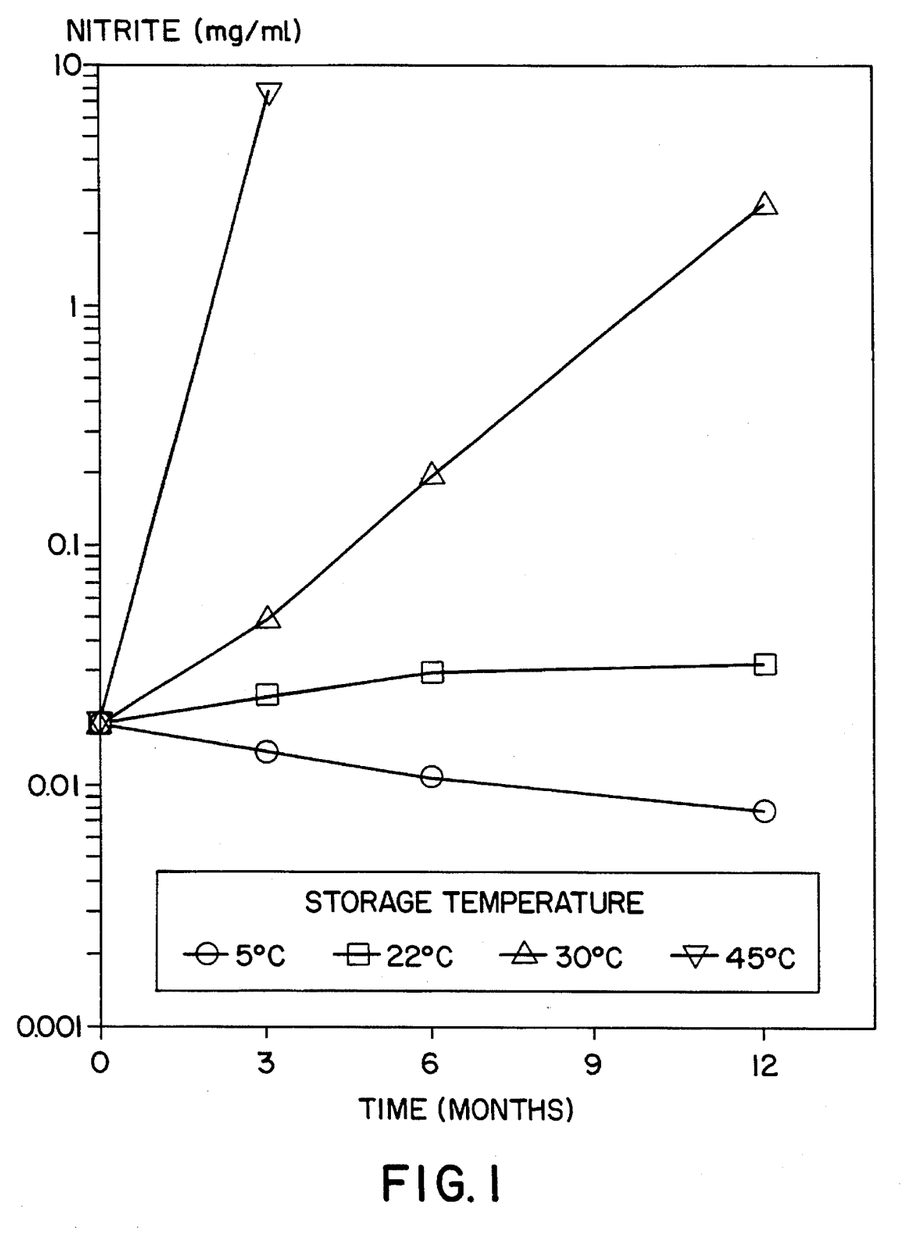
FIGS. 1 to 5 show, in graph form, results obtained for preparations according to the invention and comparison preparations in a number of series of experiments.
Figure 2:
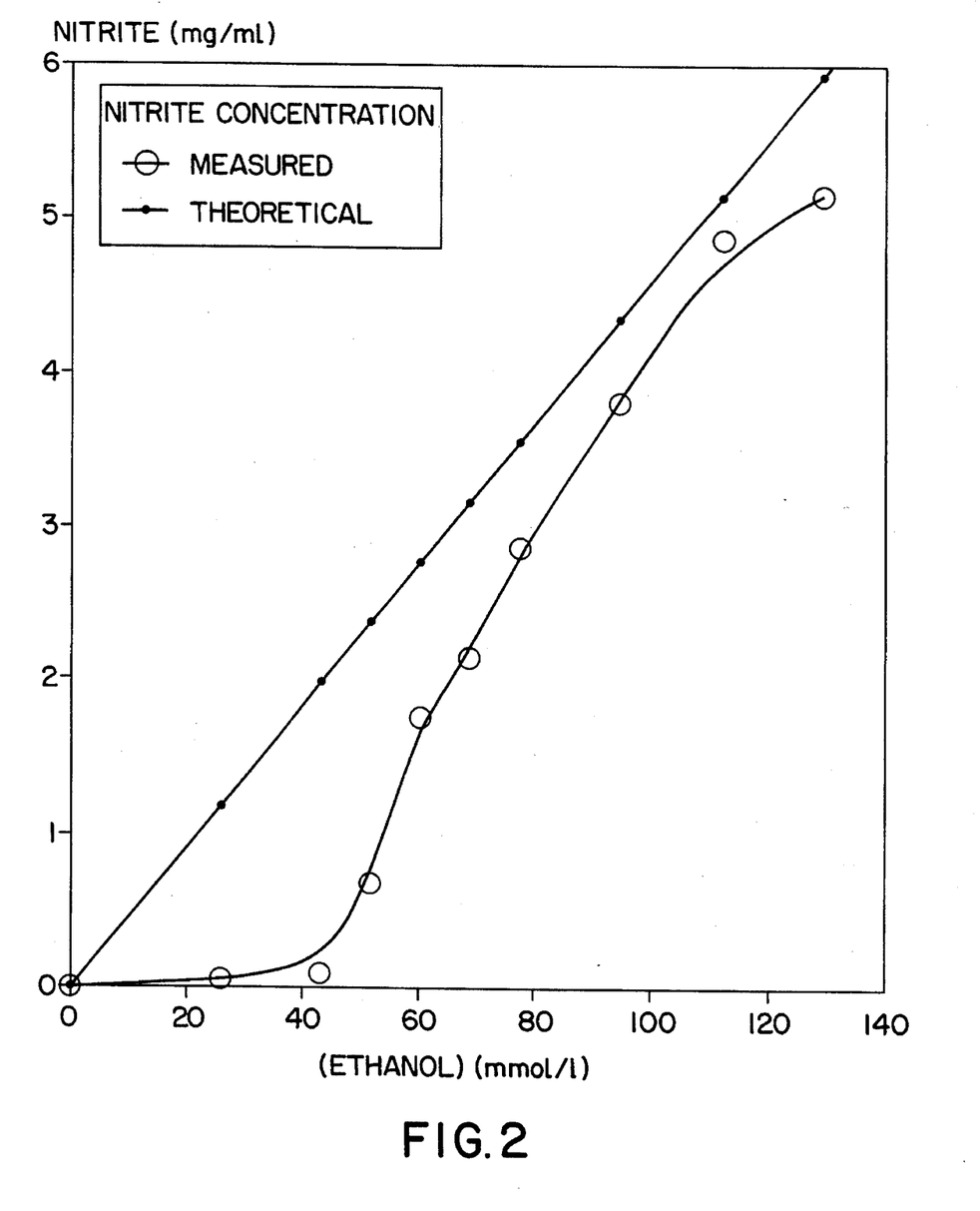

The concentration of the nitrate reduction products formed by reaction of primary $C_1$-$C_5$-alkanol with nitric acid is, in the range under investigation, essentially independent of the concentration of nitric acid, as illustrated in Examples 1 and 2. However, it is heavily dependent on the alkanol concentration employed, and in this context a nonlinear relationship has been found between the alkanol concentration and the measured nitrite concentration. As indicated in FIG. 2 and in Examples 1 and 2 for ethanol, only small quantities of nitrate reduction products are formed at ethanol concentrations of less than 45 mmol/l, and the measured nitrite concentrations are generally markedly below a concentration of 0.1 mg/ml, which reflects the beginning of therapeutic activity. If the ethanol concentration is raised further, however, there is a sharp rise in the measured nitrite concentration. The cause of this effect is not known. However, it opens up the possibility of obtaining effective preparations by reacting a $C_1$-$C_5$-alkanol with nitric acid, if the alkanol is employed in a concentration of at least 45 mmol/l, and it offers the additional possibility of supersaturating the solution with nitrous gases if the alkanol concentration is increased further.

In the hair test described in Example 3, the preparations according to the invention proved to have an effect equivalent to that of a preparation produced in identical manner with 6.4M nitric acid, and that of the commercial preparation Solcoderm. In every case a rapid yellow coloration was effected and the decomposition of the hair was suppressed, whereas an inadequate addition of alkanol or the use of pure nitric acid led to decomposition of the hair. The present invention therefore enables, surprisingly and counter to the findings of EP-A-26 532, a reduction in the concentration of nitric acid to distinctly less than 6 mol/l, while retaining the activity.

Figure 3:
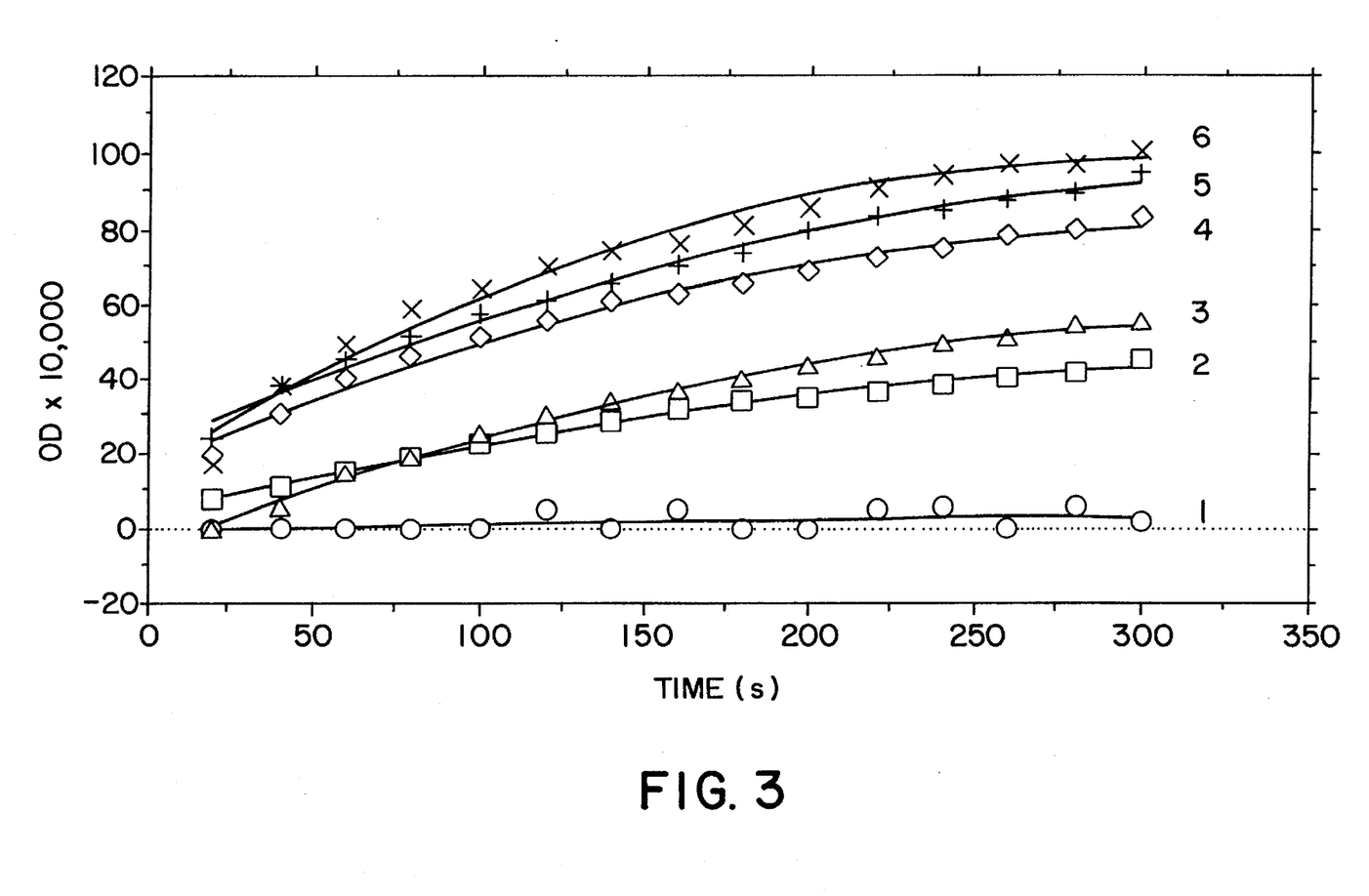
Figure 4:
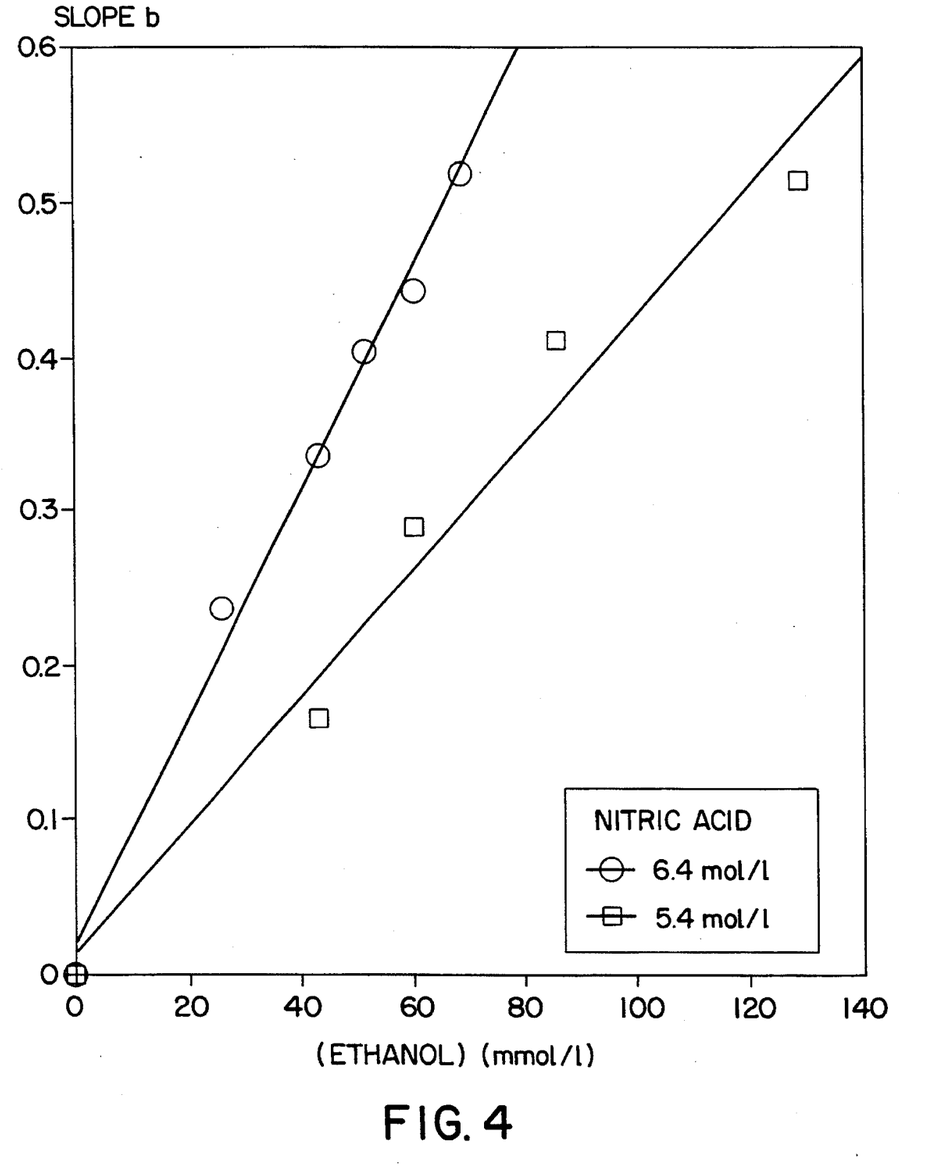
Figure 5:
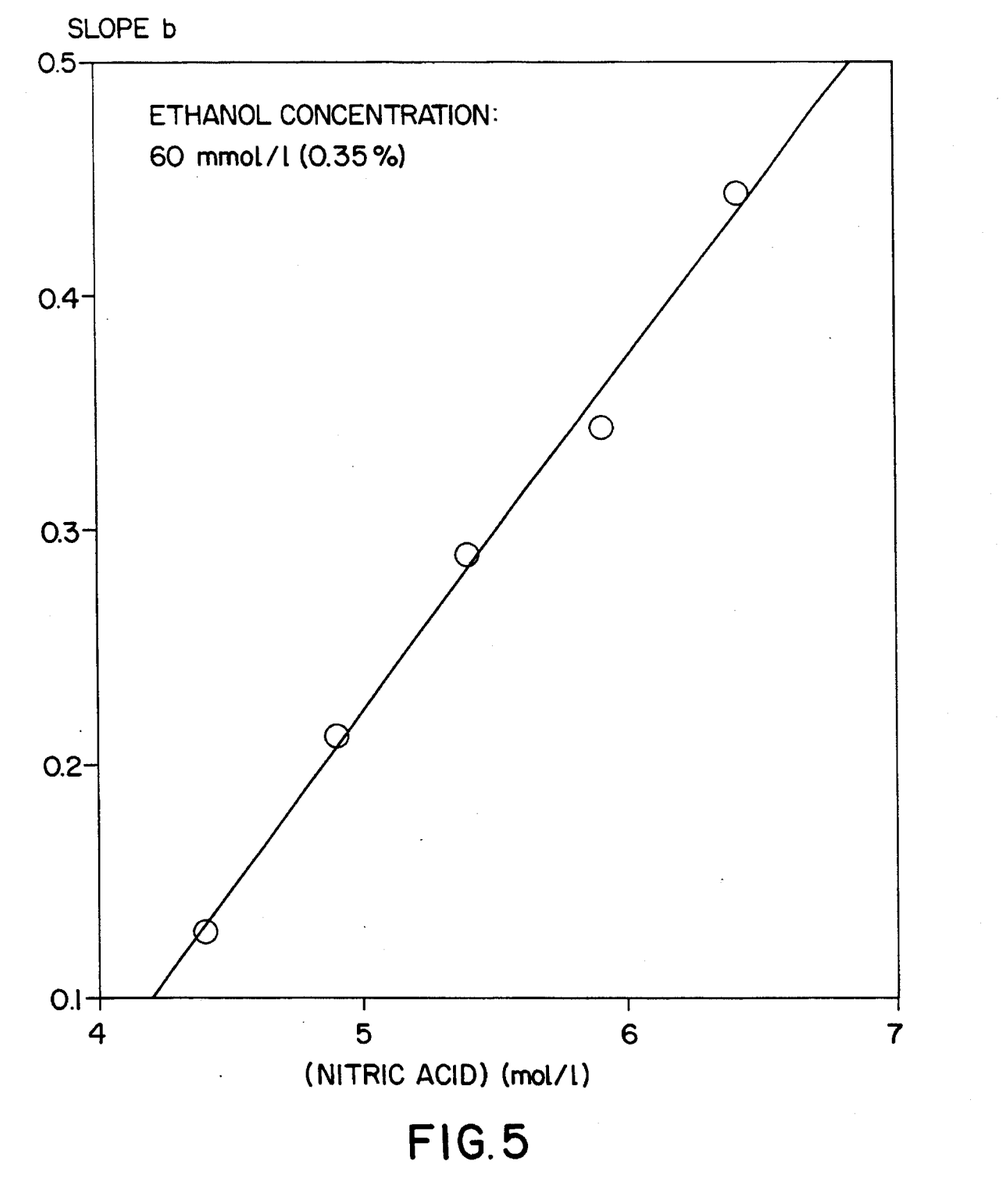

In order to ascertain more precisely any differences in the activity of the preparations, the pepsin test described in Example 4 was developed as a model for the first reaction of mummification. FIG. 3 indicates the optical densities (OD) measured in the pepsin test for samples 1–6 as a function of time. The "slope b" of the curves was used as a measure of the activity model (rapidity of discolouration). FIG. 4 shows the dependency of the slope b in the pepsin test on the ethanol concentration used in the case of 5.4M and 6.4M nitric acid. FIG. 5 shows the dependency of the slope b in the pepsin test on the nitric acid concentration, using a constant ethanol concentration of 60 mmol/l (0.35% by volume).

The preparations produced using an alkanol concentration of at least 45 mmol/l also proved to be sufficiently effective in the pepsin test. Surprisingly, however, the results show that the rapidity of discolouration in the pepsin test increases both with increasing nitric acid concentration and with increasing alkanol concentration. It follows from this finding that a reduction in the rate of discolouration, caused by a decrease in the nitric acid concentration, can largely be compensated if desired by raising the alkanol concentration, leading to a corresponding rise in the concentration of nitrate reduction products (cf. FIG. 2).

The production process according to the invention leads to a complete reaction of the alkanols, with the formation of the corresponding alkanoic acids and in some cases (especially when methanol or ethanol is used) of carbon dioxide in addition.

The alkanols are advantageously employed in a concentration of not more than approximately 170 mmol/l, preferably not more than approximately 130 mmol/l. By this means an excessive pressure is avoided if the preparations are produced under gastight closure. With regard to the results in the pepsin test, an alkanol concentration of from approximately 60 to 90 mmol/l is preferably used in general.

Correspondingly, the preparations according to the invention contain $C_1$-$C_5$-alkanoic acid in a concentration of not more than 170 mmol/l, preferably from approximately 9 to 90 mmol/l, and the concentration of nitrate reduction products, measured as nitrite, is advantageously from approximately 0.1 to approximately 6, preferably from approximately 1 to 5 and particularly preferably from approximately 2 to 4 mg of nitrite per ml.

To promote the formation of nitrate reduction products in the form of nitrose gases, in the case of production and/or storage in containers with a gastight closure, the size of the containers is preferably chosen such that the ratio of the liquid volume to the total volume of the container is not more than 1:2, particularly preferably from approximately 1:10 to 1:5. The preparations according to the invention may, for example, be produced and stored in 1 ml glass ampoules in quantities of in each case from approximately 0.1 to 0.2 ml, which are generally sufficient for a single treatment. This almost completely eliminates the disposal of excess solution and the danger of possibly applying solutions which have become inactive.

As shown by the skin test in Example 5, the preparations according to the invention do not result in any side effects even in the upper range of the nitric acid concentration, with the exception of a slight reddening and very slight blistering, which then disappears within a few hours. Even if the content of nitrate reduction products were reduced completely as a result of improper handling, the side effects would remain comparatively small because of the low concentration of nitric acid. A preparation produced in an analogous manner, with a nitric acid concentration of 6.4 mol/l, gave slightly higher side effects and proved, however, also to be better than the commercial preparation Solcoderm. In the case of both comparison preparations, however, the danger exists that relatively severe side effects, for example open wounds or ulcerations, could occur as a result of improper handling. According to the invention, therefore, the nitric acid is advantageously used in a concentration of not more than 5.5 mol/l.

The preparations according to the invention thus make possible a considerably safer application with approximately the same good activity as the known preparations, since the side effects which occur are less, a defined composition and activity exist, and the risk of side effects remains relatively low even in the case of improper handling.

The preparations according to the invention can be used in cosmetics and in medicine and are suitable for all areas of application and indications given in EP-A-26 532. They are indicated in particular for the topical treatment of superficial, benign skin changes, such as verrucas (e.g. common warts and plantar warts), benign naevi, seborrhoeic and actinic keratoses and condylomata and superficial, benign changes in the mucous membrane, for example benign cervical lesions, such as portioectopies (for example ectropium, erythroplakia and pseudoerosion), transformation zones, nabothian cysts, polyps of the cervical canal, condylomata and post-operative granulomas.

Because of their very low risk of side effects, the preparations according to the invention, unlike the preparations described in EP-A-26 532, are suitable not only for treating small-surface-area changes in skin and mucous membrane but also for treating flat lesions and infections, of large surface area, of the skin and mucous membrane, and also, in particular, for treating fungal diseases of the skin and mucous membrane, for example pedal mycosis and onychomycosis.

All preparations according to the invention are suitable in principle for the abovementioned indications. For the treatment of flat lesions of large surface area, and of fungal diseases of the skin and mucous membrane, however, it is generally preferred to use preparations which have a nitric acid concentration of from 1 to 4 mol/l. For the treatment of hyperplastic, i.e. elevated, clearly defined changes in the skin and mucous membrane, on the other hand, it is preferred to use preparations having a nitric acid concentration of from 4 to 5.5 mol/l.

Just as described in EP-A-26 532, the preparations according to the invention can be applied by topical application or other forms of local treatment, on and/or in the pathologically altered areas of tissue. As applicator, it is possible and preferred to use a small, pointed wooden stick or thin, porous plastic stick, or a brush for treating relatively large areas.

The invention is illustrated in more detail in the examples which follow. Room temperature denotes in each case a temperature of 22° C. Nitrite concentrations were in each case determined by the method described in Analyst 94, 585 (1969), by reaction with sulphanilic acid and 1-naphthylamine, and relate in each case to the overall concentration of the nitrate reduction products which can be measured as nitrite.

EXAMPLE 1

1 Part by volume of 70 per cent strength nitric acid (15.7 mol/l) and 1,907 parts by volume of water were precooled to less than 5° C. in separate vessels, in an ice bath. Subsequently the cold nitric acid was slowly added, with stirring and cooling, to the cold water, and the solution (5.4M nitric acid) was mixed for a further 15 minutes in an ice bath. Subsequently the solution was admixed with ethanol in a quantity of 60 mmol per 1 of solution and stirred. Using an ampoule-filling machine, 1 ml DIN ampoules having a breaking ring were each filled with 0.2 ml of the solution and were immediately fused. During the addition of ethanol and the entire duration of filling, the solution was maintained at 0°–2° C. in an ice bath. In samples maintained at 0°–2° C. for 24 hours no reaction was observed, so that the production of large batches is also ensured by this method.

The sealed ampoules were allowed to warm up to room temperature, the ethanol beginning to react spontaneously and completely to form acetic acid and nitrous gases. After 24 hours the residual content of ethanol, determined by means of high-pressure liquid chromatography, was distinctly below 100 ppm in each case. The resulting preparation in ampoule form, consisting of aqueous nitric acid, nitrate reduction products and acetic acid, had an acid equivalent of 5.50 mol/l and a concentration of nitrate reduction products, measured as nitrite, of 1.41 mg of nitrite per ml of solution.

In an analogous manner, but using different concentrations of ethanol and nitric acid, the preparations listed in Table 1 were produced and the nitrite concentrations indicated in the table were measured.

TABLE 1

| Ethanol concentration (mmol/l) | Nitric acid concentration (mol/l) | Nitrite concentration (mg/ml) |
| --- | --- | --- |
| 43 | 5.4 | 0.08 |
| 43 | 6.4 | 0.09 |
| 60 | 4.9 | 1.61 |
| 60 | 5.4 | 1.41 |
| 60 | 6.4 | 1.75 |
| 86 | 5.4 | 3.20 |
| 129 | 5.4 | 5.33 |
| 129 | 6.4 | 5.14 |

EXAMPLE 2

In analogy to Example 1, a 6.4M nitric acid solution was prepared from 1 part by volume of 70 per cent strength nitric acid and 1.453 parts by volume of water, and ethanol in a quantity of 60 mmol per l of solution was added to this solution, and the mixture was dispensed into ampoules and allowed to warm up to room temperature. The resulting preparation had an acid equivalent of 6.64 mol/l and a concentration of nitrate reduction products, measured as nitrite, of 1.75 mg of nitrite per ml of solution.

Within the scope of accurate measurement, the concentration of nitrate reduction products was found to be substantially independent of the concentration of nitric acid (cf. Example 1 and Table 1), as was expected on the basis of the high excess of nitric acid and the complete oxidation of the ethanol.

In the same way as described above, but using different concentrations of ethanol within the range from 0–130 mmol/l, further preparations were produced and in each case the concentration of nitrate reduction products, measured as nitrite, in the solution was determined. The measured nitrite concentrations are shown in graph form in FIG. 2 as a function of the ethanol concentration used. For comparison, the theoretically possible nitrite concentrations are also drawn in, which were calculated under the assumption that nitrate reduction products which can be measured in the solution as nitrite are formed exclusively from nitrate in the reaction with ethanol.

FIG. 2 shows that the measured nitrite concentrations do not increase linearly as the ethanol concentration rises. At ethanol concentrations of below 45 mmol/l, only small quantities of nitrate reduction products were found; the measured nitrite concentrations were markedly below the value of 0.1 mg of nitrite per ml, which reflects the beginning of therapeutic activity. Above an ethanol concentration of 45 mmol/l, however, there was a sharp rise in the nitrite concentration as the ethanol concentration rose, indicating a supersaturation of the solution with nitrous gases.

EXAMPLE 3

(Hair test)

In analogy to Example 1, using the concentrations of nitric acid and of ethanol indicated in Table 2, a number of preparations were produced and their action on human hair was investigated. For this purpose, blond human hair was washed with a solution of 1% by volume of acetone in water and then with water and dried. The hair degreased in this manner was chopped up finely. Subsequently, in each case 10 mg of the hair were added to 1 ml of the preparation, and the action was assessed visually on the basis of the yellow coloration which occurs and any decomposition taking place. The change in colour signals a chemical reaction with the preparation, whereby the tissue loses its vitality but substantially retains its anatomical structure except for any decomposition. The action of the commercial preparation Solcoderm was tested likewise, for comparison.

TABLE 2

(human hair)

| Nitric acid concentration (mol/l) | Ethanol concentration (mmol/l) | Yellow coloration begins after | Decomposition |
| --- | --- | --- | --- |
| 6.4 | 0 | 2 h | after 18 h |
| 5.4 | 0 | 8 h | after 18 h |
| 6.4 | 26 | 2 min | after 18 h |
| 5.4 | 26 | 2 min | after 18 h |
| 6.4 | 60 | 2 min | no |
| 5.4 | 60 | 2 min | no |
| 4.9 | 60 | 2 min | no |
| 5.4 | 86 | 2 min | no |
| Solcoderm | | 2 min | no |

Samples without added ethanol gave a yellow coloration only after a long delay, and the hair subsequently decomposed; the yellow coloration was also delayed by reducing the concentration of nitric acid. The use of 26 mmol of ethanol per l in 6.4M or 5.4M nitric acid resulted in a rapid yellow coloration but led finally, likewise, to decomposition of the hair. The samples produced using an ethanol concentration of 60 or 86 mmol/l gave, for all concentrations of nitric acid investigated, a rapid yellow coloration without decomposition of the hair. Differences in the rapidity of the yellow coloration of the samples were not observed; from this point of view the hair test proved to be too insensitive.

The nitrate reduction products formed by reaction of ethanol with nitric acid therefore bring about a considerable acceleration in the reaction with the tissue and, consequently, a distinctly improved action. Above a certain threshold value of nitrate reduction products, in addition, the decomposition of the tissue is suppressed, i.e. the presence of nitrate reduction products in a sufficient quantity ensures the fixation of the anatomical structure (mummification) and reduces the risk of side effects.

EXAMPLE 4

(pepsin test)

Analogously to Example 1, using the nitric acid and ethanol concentrations indicated in Table 3 and in FIGS. 4 and 5, a number of preparations were produced and were subsequently tested for their action with a pepsin solution. The pepsin test was developed as a model for the first reaction of mummification (reaction with primary and secondary amino groups, which manifests itself in a discoloration of the solution) and permits a more precise quantification of this action than the yellow coloration in the hair test.

To carry out the pepsin test, in each case 100 µl of the sample were added, exactly 1 minute after the ampoule was opened, to a solution of 1 mg of pepsin in 1 ml of water. The ensuing reaction was monitored spectrophotometrically with regard to the time-dependent discoloration of the mixture. The parameter measured was in each case the optical density at a wavelength of 438 nm over a period of 300 seconds from the addition of the sample to the pepsin solution. The first measurement was made in each case 20 seconds after the addition. The optical densities measured were evaluated, for each sample as a curve, with the equation $$y = a + bx + cx^2 \quad (1)$$

in which y is the optical density and x is the time in seconds and the parameters a, b and c were calculated. The rapidity of the discoloration is determined essentially by parameter b—referred to as "slope b" in the context of the present invention—which was therefore taken as a measure for the model of action.

Sample nos. 1 to 10 gave the values for the slope b as indicated in Table 3. For comparison, the commercial preparation Solcoderm was also investigated in the pepsin test.

TABLE 3

(Pepsin test)

| Sample No. | Nitric acid concentration (mol/l) | Ethanol concentration (mmol/l) | Slope b |
| --- | --- | --- | --- |
| 1 | 6.4 | 0 | 0 |
| 2 | 4.9 | 60 | 0.212 |
| 3 | 5.9 | 60 | 0.344 |
| 4 | 6.4 | 51 | 0.404 |
| 5 | 5.4 | 86 | 0.411 |
| 6 | 6.4 | 60 | 0.443 |
| 7 | 3.4 | 129 | 0.223 |
| 8 | 4.4 | 129 | 0.340 |
| 9 | 5.4 | 129 | 0.514 |
| 10 | 6.4 | 129 | 0.705 |
| Solcoderm | | | 0.316 |

FIG. 3 shows, in graph form, the optical densities (OD) measured for sample nos. 1 to 6 as a function of the time.

The result of sample no. 1 confirms that preparations produced without the addition of ethanol are inactive. Sample nos. 2 to 6 showed a good action which apparently increases both with increasing nitric acid concentration and with increasing ethanol concentration.

FIG. 4 shows, in graph form, the slope b values of preparations produced using variable ethanol concentrations and a constant nitric acid concentration of 5.4 or 6.4 mol/l. As is evident from FIG. 4, the slope b values were approximately proportional to the ethanol concentrations used. Preparations with 5.4M nitric acid gave a less steep curve; this effect can, however, be compensated by raising the ethanol concentration correspondingly.

FIG. 5 shows, in graph form, the slope b values of preparations produced with a constant ethanol concentration of 60 mmol/l and a variable nitric acid concentration in the range from 4.4–6.4M. As can be taken from the FIGURE, the slope b values within this concentration range experience an approximately linear increase as the concentration of nitric acid rises.

EXAMPLE 5

(Test on human skin)

To assess the side effects on normal human skin, two preparations, which were produced in accordance with Example 1 from nitric acid (6.4 and 5.4 mol/l respectively) and ethanol (60 and 86 mmol/l respectively) and, for comparison, corresponding and more heavily diluted nitric acid solutions without the addition of ethanol, and the commercial preparation Solcoderm, were applied to the underside of the forearm and allowed to act for 5 minutes. Samples with nitric acid concentrations of 5.4 mol/l or less were applied in a quantity of 40 µl, the other samples in a quantity of 20 µl. The action was observed over a period of 36 hours and resulted in the picture indicated in Table 4.

TABLE 4

(human skin, underside of forearm)

| | straight after action | after 1 h | after 7 h | after 36 h |
| --- | --- | --- | --- | --- |
| 6.4 M nitric acid (20 µl) | severe reddening large blister formed | | open blister | open wound |
| 5.4 M nitric acid (40 µl) | severe reddening blister formed | | blister remains closed | |
| 4.4 M nitric acid (40 µl) | moderate reddening small blister formed | | blister remains closed | blister disappeared |
| 3.4 M nitric acid (40 µl) | moderate reddening small blister formed | | blister remains closed | blister disappeared |
| 2.4 M nitric acid (40 µl) | slight reddening | | very slight reddening | no reddening |
| 1.4 M nitric acid (40 µl) | very slight reddening | no reddening | | |
| Solcoderm (20 µl) | Severe reddening with brownish edges blister formed | | blister remains closed | |
| 6.4 M nitric acid + 60 mmol/l ethanol (20 µl) | distinct brown coloration with slight reddening small blister formed | | blister remains closed | blister disappeared |
| 5.4 M nitric acid + 86 mmol/l ethanol (40 µl) | distinct brown coloration with slight reddening very slight blistering | | blister disappeared | |

Despite application of twice the volume, 5.4M nitric acid gave lesser side effects than 6.4M nitric acid and, in particular, did not result in the formation of an open wound. As the concentration of nitric acid reduced further, a further reduction was observed in the side effects. In particular, at 2.4M and 1.4M nitric acid there was no longer any blistering. Solcoderm gave a similar reaction to that of 5.4M nitric acid. The two preparations produced with the addition of ethanol led, in comparison to the corresponding, pure nitric acid solutions, to distinctly lesser side effects which, in addition, subsided rapidly; in other words, the nitrate reduction products formed in these preparations by reaction with ethanol suppressed the side effects of nitric acid on normal tissue to a substantial extent. Furthermore, both preparations proved to be markedly better than Solcoderm.

The preparation produced from 5.4M nitric acid and ethanol in a concentration of 86 mmol/l exhibited similarly low side effects as those of pure 2.4M nitric acid. This enables safe application, since the side effects remain comparatively low even if the content of nitrate reduction products decreases or completely disappears as a result of improper handling. A control experiment with a sample (20 μl) which was not applied to the skin until 24 hours after the ampoule had been opened, and whose action was likewise observed over a period of 36 hours, gave severe reddening with brownish spots, and the formation of blisters which remained closed. Since the risk of side effects decreases still further as the nitric acid concentration is reduced, such preparations are also suitable for treating large-surface-area diseases of the skin and mucous membrane.

EXAMPLE 6

A preparation produced analogously to Example 1 and using a nitric acid concentration of 5.4 mol/l and an ethanol concentration of 86 mmol/l (measured nitrite content: 3.20 mg/ml) was investigated with regard to its action in the pepsin test over a period of 30 minutes from the ampoule being opened. The pepsin test was carried out as described in Example 4. The results are compiled in Table 5.

TABLE 5

| Time after opening (min) | Slope b | Slope b as % of initial value |
| --- | --- | --- |
| 0.3 | 0.506 | 100 |
| 1 | 0.483 | 95 |
| 3 | 0.392 | 77 |
| 6 | 0.289 | 57 |
| 10 | 0.239 | 47 |
| 23 | 0.221 | 44 |
| 30 | 0.167 | 33 |
| 54 | 0.102 | 20 |

The application of the preparation within a few minutes up to one hour, preferably within half an hour, after the ampoule had been opened guarantees the therapeutic activity and the substantial freedom from side effects.

EXAMPLE 7

Using the ethanol and nitric acid concentrations indicated in Table 6, a number of preparations were produced as described in Example 1 and, after the ampoules had been fused, were stored at 22° C. After various storage times, the acetic acid content of the preparations was determined by means of gas-chromatographic analysis. Control measurements using an enzymatic method (acetate test kit from Boehringer) gave results which were consistent within the bounds of accurate measurement.

TABLE 6

| Ethanol concentration (mmol/l) | Nitric acid concentration (mol/l) | Acetic acid concentration (mg/ml) | Storage time at 22° C. |
| --- | --- | --- | --- |
| 43 | 5.4 | 0.55 | 15 months |
| 43 | 6.4 | 0.93 | 19 months |
| 60 | 4.9 | 0.61 | 21 days |
| 60 | 4.9 | 0.59 | 16 months |
| 60 | 5.4 | 0.93 | 21 days |
| 60 | 5.4 | 0.90 | 16 months |
| 60 | 6.4 | 1.63 | 27 days |
| 60 | 6.4 | 1.56 | 16 months |
| 86 | 5.4 | 1.57 | 23 hours |
| 86 | 5.4 | 1.55 | 27 days |
| 86 | 5.4 | 1.63 | 13 months |
| 129 | 5.4 | 2.92 | 14 months |
| 129 | 6.4 | 4.63 | 21 months |

The results confirm that the acetic acid concentration remains constant even on prolonged storage and that an increase in the ethanol concentration employed leads to a higher acetic acid concentration. The measured acetic acid concentrations, are, however, lower than the ethanol concentrations employed. By means of a barium chloride test, carbon dioxide was detected as a further reaction product of ethanol. In the fully reacted solutions, neither ethanol nor other reaction products were detected; in other words, ethanol was converted completely to acetic acid and carbon dioxide.

EXAMPLE 8

In analogy to Example 1, 5.4M nitric acid was admixed with ethanol in a quantity of 86 mmol per l of solution, and the solution was dispensed into a number of ampoules. The solutions in ampoule form were stored for 14 days or 1 month at various temperatures and were then investigated for their content of acetic acid and nitrate reduction products. The results are listed in Table 7. They confirm that the storage temperature within the range under investigation has no significant effect on the composition of the preparation.

TABLE 7

| Storage conditions | | Nitrite concentration (mg/ml) | Acetic acid concentration (mg/ml) |
| --- | --- | --- | --- |
| 14 days at | 22° C. | 2.35 | 1.42 |
| | 30° C. | 2.55 | 1.42 |
| | 40° C. | 2.32 | 1.39 |
| | 50° C. | 2.47 | 1.42 |
| 1 month at | 22° C. | 2.37 | 1.43 |
| | 30° C. | 2.22 | 1.44 |
| | 40° C. | 2.27 | 1.42 |
| | 50° C. | 2.81 | 1.40 |

EXAMPLE 9

(Treatment of common and plantar warts)

To carry out a clinical study on the treatment of common and plantar warts, the following preparations were produced by the method described in Example 1:

TABLE 8

| Preparation | Ethanol concentration (mmol/l) | Nitric acid concentration (mol/l) |
| --- | --- | --- |
| A | 60 | 5.4 |
| B | 86 | 5.4 |
| C | 129 | 4.4 |

A total of 26 warts (22 patients) were treated with one of preparations A–C and, in the case of patients with two similar types of wart, moreover, one wart was treated with Solcoderm for comparison. The preparations were applied using a small, thin, porous plastic stick, by distributing the preparation dropwise on the lesion using the small plastic stick, and incorporating it into the lesion by gentle pricking. This treatment was in each case continued until the lesion had undergone a uniform yellow discolouration and/or until slight burning was felt. Preparations A–C led in each case to discoloration of the lesion within approximately 3 to 5 minutes, Solcoderm within approximately 10 minutes. Similarly, a hot sensation and prickling occurred with preparations A–C more rapidly (within approximately 5 to 10 minutes) than with Solcoderm (within 15 to 30 minutes). The duration of treatment with preparations A–C was thus distinctly shorter and, in addition, the sensation of pain, with respect to its intensity and duration, was less than in the case of treatment with Solcoderm. At intervals of from 4 to 8 days the treatment was repeated one or more times, insofar as the lesion had not completely healed. The results are compiled in Table 9.

TABLE 9

| Indication/ preparation | Total cases | after 1 treatment | Healing after 2 treatments | Incomplete after 2 treatments |
| --- | --- | --- | --- | --- |
| Common warts | | | | |
| B | 4 | — | 2 | 2 |
| C | 7 | 3 | 2 | 2 |
| Plantar warts | | | | |
| A | 5 | 2 | 2 | 1 |
| B | 6 | 1 | 3 | 2 |
| C | 4 | 1 | 1 | 2 |

Of the cases listed in Table 9 in which the lesion was still not completely healed after 2 treatments, one of the common warts treated with preparation B was cured after the 3rd treatment, one of the plantar warts treated with preparation B was cured after the 3rd treatment and the other after the 4th treatment, and one of the plantar warts treated with preparation C was healed completely after the 3rd treatment. The other cases were still being treated at the time the intermediate report was compiled.

Four common warts and two plantar warts were treated with the comparison preparation, of which warts 2 common warts and one plantar wart were healed after 1 treatment and 2 common warts and one plantar wart after the second treatment.

EXAMPLE 10

(Pedal mycosis treatment)

In one case study, one patient with pedal mycotic infestation on both feet was treated with a preparation according to the invention which had been produced by the method described in Example 1, from 5.4M nitric acid and 86 mmol of ethanol per 1 of solution.

One foot had severe mycotic infestation between the fourth and fifth toes, with instances of skin detachment and severe reddening. When the toes were spread the thin remaining skin tore, leading to bleeding. After unsuccessful treatment with an oxiconazole preparation (Oceral, Roche), approximately 100 μl of the preparation according to the invention were applied to the lesion, the patient feeling a short, stinging burning sensation for a few seconds at the damaged areas of skin, and certain sharply defined areas around the damaged areas of skin undergoing a brown discoloration. The large remainder of the affected skin and the healthy skin surrounding it displayed no discoloration or only a slight yellow coloration. 8 hours after the treatment, the treated skin continued to show severe reddening, and the patient still felt a slight pain on pressure, but no longer any pain at rest. The lesion was subsequently treated overnight with a wound-healing ointment (Solcoseryl ointment, Solco Basel AG). After 3 days the skin lesions typical of pedal mycosis had disappeared; the surface of the skin was hard and taut. After 7 days the affected area had healed completely, and there was no recurrence.

The other foot exhibited slight mycotic infestation without torn skin. The affected areas were treated with the preparation according to the invention, with no pain occurring. After 7 days the lesion had completely healed, and there was likewise no recurrence.

EXAMPLE 11

(Onychomycosis treatment)

In a further case study, a patient with onychomycosis (total infestation of the ring, middle and index fingernails of the right hand) was treated with a preparation according to the invention produced by the method described in Example 1, from 3.4M nitric acid and 129 mmol of ethanol per 1 of solution. Prior to this treatment, the affected nails were treated with an amorolfine preparation (Loceryl-Lack, Roche), with neither reduction of the mycotic infestation nor nail growth being observed.

The preparation according to the invention was applied to the affected nails, a distinct yellow-brown coloration appearing within a minute. The patient felt no pain, except for a slight burning lasting approximately 3 minutes at a point where the skin, on transition from the nail bed to the normal skin, had a small injury. After 3 days, portions of nail which were infected particularly severely crumbled away. The treatment with the preparation according to the invention was repeated approximately every 7 days. After just 14 days, a distinct improvement in the nails (lesser degree of destruction) was observed. After 2 months regrowth of the nails was observed; the rear portion of the nail, adjoining the nail bed, however, was still affected as a result of mycotic infestation in the nail bed itself. The preparation according to the invention is therefore suitable for treating superficial onychomycotic infections; in the case of infection of the nail bed, however, therapy must be carried out together with an oral antimycotic.

We claim:

1. A stable and reproducible composition based on an aqueous solution of nitric acid, containing nitrate reduction products, for the local treatment of superficial changes in skin and mucous membrane and of superficial infections of the skin and mucous membrane, characterized in that said composition consists essentially of 1–5.5M aqueous nitric acid, nitrate reduction products in a concentration corresponding to from 0.1 to 6 mg of nitrite per ml of solution, and $C_1$-$C_5$-alkanoic acid in a concentration of not more than 170 mmol per 1 of solution, said composition being enclosed in a container with a gastight closure and having constant concentrations of the nitric acid, nitrate reduction products and alkanoic acid which are essentially independent of temperature and storage time.

2. The composition according to claim 1 for the treatment of hyperplastic changes in skin and mucous membrane, characterized in that it has a nitric acid concentration of 4–5.5M.

3. The composition according to claim 1 for the treatment of fungal diseases of the skin and mucous membrane, characterized in that it has a nitric acid concentration of 1–4M.

4. The composition according to one of claims 1 to 3, characterized in that the concentration of nitrate reduction products corresponds to from 1 to 5 mg of nitrite per ml of solution.

5. The composition according to claim 4, characterized in that the concentration of nitrate reduction products corresponds to from 2 to 4 mg of nitrite per ml of solution.

6. The composition according to claim 1, characterized in that the concentration of $C_1$-$C_5$-alkanoic acid is at least 5 mmol per l.

7. The composition according to claim 6, characterized in that the concentration of $C_1$-$C_5$-alkanoic acid is from 9 to 90 mmol per l.

8. The composition according to claim 1, characterized in that it contains acetic acid as $C_1$-$C_5$-alkanoic acid.

9. The composition according to claim 1, characterized in that the composition is enclosed in a sealed ampoule.

10. The composition according to claim 1, characterized in that the ratio of the liquid volume to the total volume of the container is not more than 1:2.

11. The composition according to claim 10, characterized in that the ratio of the liquid volume to the total volume of the container is from 1:10 to 1:5.

12. Process for the production of a composition according to claim 1, characterized in that 1–5.5 M aqueous nitric acid is reacted with a primary $C_1$–$C_5$-alkanol in a quantity of from 45 to 170 mmol per l of nitric acid.

13. Process according to claim 12, characterized in that from 60 to 90 mmol of the primary $C_1$–$C_5$-alkanol are used per l of nitric acid.

14. Process according to claim 12 or 13, characterized in that ethanol is used as primary $C_1$–$C_5$-alkanol.

15. Process according to claim 12 or 13, characterized in that the nitric acid and the primary $C_1$–$C_5$-alkanol are mixed at a temperature below the reaction temperature and the mixture in a container with a gastight closure, is heated to reaction temperatue or above.

16. Process according to claim 15, characterized in that the nitric acid is mixed with ethanol at a temperature of not more than 10° C. and the mixture in a container with a gastight closure is heated to from 20° to 40° C.

17. Process according to claim 15, characterized in that the gastight closure is a sealed ampoule.

18. Process according to claim 16, characterized in that the mixture is heated to room temperature.

* * * * *

UNITED STATES PATENT AND TRADEMARK OFFICE
CERTIFICATE OF CORRECTION

PATENT NO. : 5,573,786
DATED : November 12, 1996
INVENTOR(S) : Michael GRABO, Christian STÄHLI, Rudolf MEYER, René GLAUSER and Murray WEINER

It is certified that error appears in the above-indentified patent and that said Letters Patent is hereby corrected as shown below:

On the title page,
In item (75) in the heading of the patent, correct the spelling of the name of the second inventor to read --Christian Stähli--.

Signed and Sealed this

Twenty-fifth Day of March, 1997

BRUCE LEHMAN

Attest:

Attesting Officer

Commissioner of Patents and Trademarks